United States Patent [19]

Keith

[54] RESTRICTION/LIGATION LABELING FOR PRIMER INITIATED MULTIPLE COPYING OF DNA SSEQUENCES

[75] Inventor: Douglas H. Keith, Oakland, Calif.

[73] Assignee: Applied Biosystems, Inc., Foster City, Calif.

[*] Notice: The portion of the term of this patent subsequent to Mar. 3, 2009 has been disclaimed.

[21] Appl. No.: 601,962

[22] Filed: Oct. 22, 1990

Related U.S. Application Data

[63] Continuation-in-part of Ser. No. 148,757, Jan. 26, 1988, Pat. No. 5,093,245.

[51] Int. Cl.$^5$ .......................... C12N 15/10; C12Q 1/68
[52] U.S. Cl. ......................................... 435/91.2; 435/6
[58] Field of Search ...................... 435/6, 91, 810, 91.2

[11] Patent Number: 5,366,877

[45] Date of Patent: *Nov. 22, 1994

[56] References Cited

U.S. PATENT DOCUMENTS

| | | | |
|---|---|---|---|
| 4,672,040 | 6/1987 | Josephson | 436/526 |
| 4,920,061 | 4/1990 | Poynton et al. | 436/526 |
| 5,093,245 | 3/1992 | Keith et al. | 435/91 |

OTHER PUBLICATIONS

Kempe et al. (1985), Nucl. Acids Res. 13(1): 45–57.

*Primary Examiner*—Richard A. Schwartz
*Assistant Examiner*—Philip W. Carter
*Attorney, Agent, or Firm*—Richard Neeley

[57] ABSTRACT

Sample DNA is analyzed by joining dsDNA sample fragments to labeling moieties having a primer binding sequence, to provide labeled dsDNA. After denaturation of the labeled dsDNA, strands binding to a probe are separated, conveniently using particles and a specific binding pair, followed by amplification of the sample strands and analysis and/or isolation of the amplified strands.

13 Claims, 4 Drawing Sheets ds DNA restriction fragment
shown with First Strand
ligated in place

Fill in with
polymerase + dNTPs

+ ▭
Displaced
Ligaid

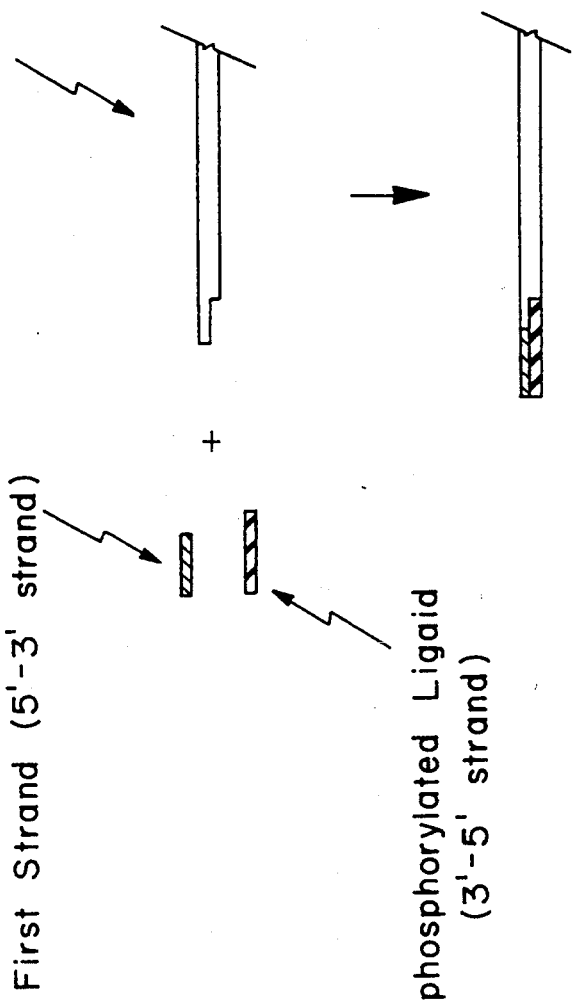

RESTRICTION/LIGATION LABELING FOR PRIMER INITIATED MULTIPLE COPYING OF DNA SSEQUENCES

CROSS-REFERENCE TO RELATED APPLICATIONS

This application is a continuation-in-part of application Ser. No. 148,757 filed Jan. 26, 1988, now U.S. Pat. No. 5,093,245, whose disclosure is incorporated herein by reference.

INTRODUCTION

1. Technical Field

Method for labeling nucleic acid fragments for detection.

2. Background

Today, biology is in many ways the science of proteins and nucleic acids. Nucleic acids are found in all living matter. For each species or host, unique sequences exist providing for the genotype and phenotype of that particular host. Thus, one can use the presence of a particular sequence as indicative of the particular strain or species. In many instances, a number of strains will share a common sequence as distinct from other strains or species, so that one can not only detect a particular strain but, if desired, can detect subspecies, species or genera. In addition, one can distinguish between RNA and DNA so as to determine whether a particular gene is being expressed, the existence of one or more alleles, the level of expression, and the like. Where cells, such as B-cells and T-cells, are involved with genomic rearrangements, one can detect the presence or absence of such rearrangements by employing probes. Thus, the detection of particular nucleic acid sequences is a powerful tool in the diagnosis of disease states, the presence of sets or subsets of cells, the particular strain or species of a pathogen, such as a bacterium, protista, virus, or the like.

The detection and isolation of sequences is also important in the field of molecular biology. Thus, the use of probes allows for detection of a variety of sequences of interest, including structural genes, regulatory sequences, introns, exons, leader sequences, sequences that are both translated and untranslated, and the like.

There is also substantial interest in detecting sequences in genetic engineering. Monitoring levels of transcription, detecting the integrity of constructs, monitoring levels of mutation, resection, mapping, or the like, provide opportunities for nucleic acid screening and detection.

In many instances, the sequence of interest may be present as only a very small fraction of the total amount of nucleic acid, and/or in very small amount, e.g., attomole or subattomole levels. Furthermore, the sequence of interest may be accompanied by a number of sequences having substantial homology to the sequence of interest. Thus, relatively high stringencies may be required to ensure the absence of unwanted heteroduplexing, which may further limit the effective detection of the sequence of interest.

Additionally, the same or similar sequences may appear on nucleic acid fragments of different size and the appearance of a sequence on a particular size fragment may be correlated to the presence of a particular phenotype.

There is also interest in developing analytical systems which can be automated, so as to minimize the time and energy required from technicians, as well as minimizing errors which may result from manual manipulation. In many systems the sample is labeled to allow for detection of the sequence. The labeling can be time consuming and limited as to the nature of the label as in nick translation with radioactive nucleotide triphosphates. In other situations, the particular nature of the label may be limited, as when using terminal deoxytransferase. Other techniques result in random substitution. There is therefore an interest in providing for rapid, conveniently controlled labeling and detection of sample nucleic acids, where the labeled moiety may be commercially available and require little, if any, technical skills, in being used to label the sample.

Relevant Literature

Kempe et al., Nucl. Acids. Res. (1985) 13:45-57 describe biotinylated oligonucleotide linked to DNA fragments by a ligase. Gamper et al., Nucl. Acids Res. (1985) 14:9943-9954, employ a psoralen-functionalized oligomer as a probe which labels target DNA when hybridization and photochemical cross-linking occur. Zapolski et al., Electrophoresis (1987) 8:255-261 discuss a robotic system for automating Southern-type nucleic acid hybridization analysis. Goldkorn and Prockop, Nucl. Acids Res. (1986) 14:9171-9191 describe techniques for covalent attachment of DNA probes to cellulosic supports for hybridization-restriction analysis. Syvanen et al., Nucl. Acids Res. (1986) 14:5037-5048 quantify nucleic acid hybrids by affinity-based hybrid collection. Forster et al., Nucl. Acids Res. (1985) 13:745-761 covalently label nucleic acids with biotin photochemically. Kinzler and Vogelstein (1989) Nucl. Acids Res. 17:3645-3653 describe the application of PCR to the identification of sequences bound by gene regulatory proteins. Roux and Dhanaragan, (1990) Biotechniques 8:48-57, 1990, Frohman et al., (1988) PNAS USA 85:8998-9002, and Loh et al. Science (1989) 243, 217-220 describe amplification techniques.

See also EPA Serial No. 89/400220.3 and U.S. Pat. Nos. 4,683,195; 4,683,202, 4,800,159 and 4,889,818.

SUMMARY OF THE INVENTION

Double-stranded DNA ("dsDNA") fragments are labeled with detectable double-stranded nucleic acid moieties that possess termini complementary to the termini of the double-stranded DNA fragments to be labeled. The labeling double-stranded moiety contains a sequence that can subsequently be utilized as a primer binding site. The labeling reaction is performed in a manner which provides for the labeling moiety to be joined to both termini of the dsDNA fragments, wherein the 5'-3' strand of the labeling moiety is ligated to the adjacent 5' end of the dsDNA fragment strand and the 3'-5' strand of the labeling moiety is covalently attached by ligation or fill-in reactions. After denaturation, strands selected by hybridizing to a probe are separated, amplified, and the presence of the target sequence is established and/or the DNA isolated.

BRIEF DESCRIPTION OF THE DRAWINGS

FIGS. 1a, 1b, 1c, and 1d are diagrams of methods of covalently attaching a labeling moiety to dsDNA sample fragments.

DESCRIPTION OF THE SPECIFIC EMBODIMENTS

Figure 1A:
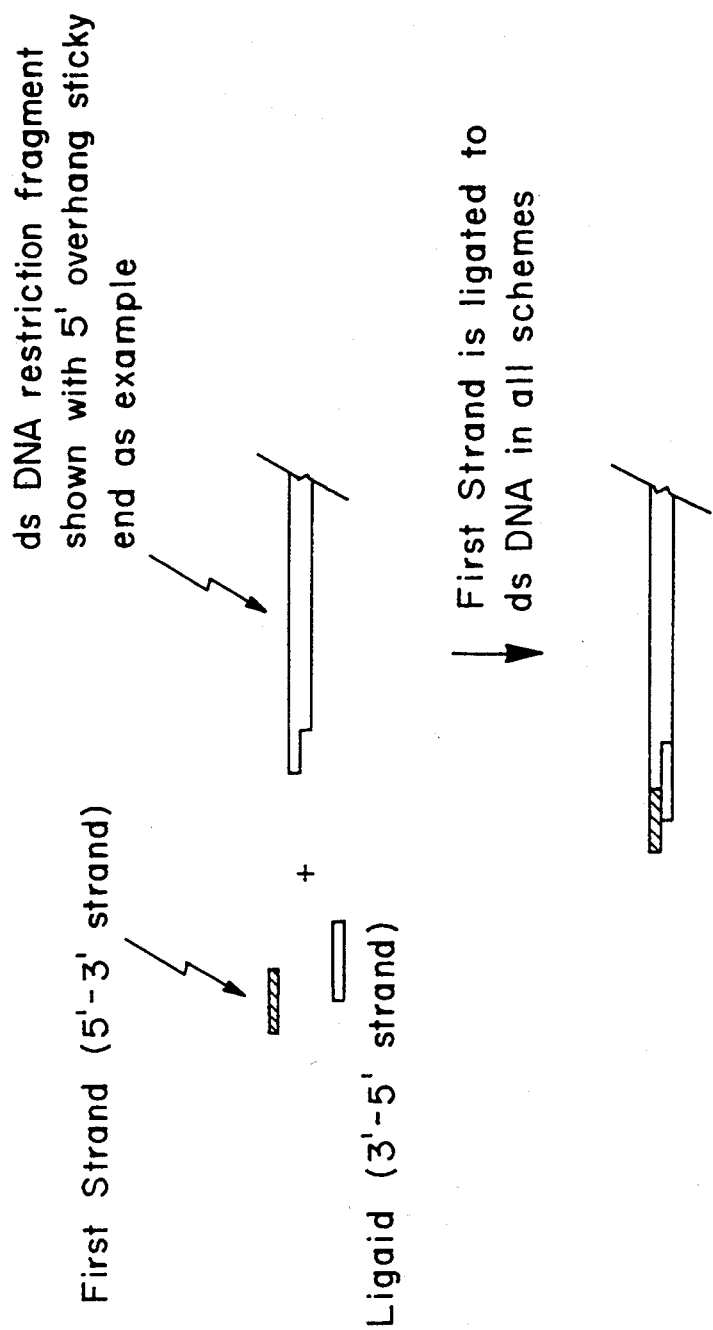

Methods and compositions are provided for producing high levels of nucleic acid strands of a target sequence, particularly for identification of the sequence in a complex mixture of nucleic acid fragments. The labeling moiety will comprise a 5'-3' strand, which is normally not phosphorylated at its 3' end, and may be ligated to the phosphorylated 5' end of the fragments of the dsDNA. The labeling moiety will also comprise a 3'-5' strand, which will usually be phosphorylated at its 5' end before combining the labeling moiety with the dsDNA fragments or may be created by filling in with a polymerase and dNTP's or may be replaced with a full length 3'-5' strand which is phosphorylated at its 5' end which is subsequently ligated. The labeling procedure results in target dsDNA fragments joined at both ends to both strands of dsDNA labeling moieties to provide symmetrical termini. After selecting those labeled sequences having a target sequence by means of a probe, such selected sequences are then separated and amplified and the presence of the target sequence may then be further established and/or the DNA isolated.

The strategy for analysis of a dsDNA sample provides for simultaneous or consecutive restriction of a dsDNA sample and tagging or labeling with oligomeric labeling dsDNA moieties as described above. The labeling moieties comprise a primer binding site. DNA to be used as a probe is joined to a separation means, which may be one member of a specific binding pair, with the other member bound to a separable support. The probe DNA and the labeled sample DNA are denatured and hybridized and sequence homologous to the probe DNA separated. After remaining non-specifically bound DNA is removed, the target DNA may be directly detected by a gel scanner, but will usually be amplified and detected.

The subject method finds use in a number of situations. The subject method can be used for detection of a target sequence to identify the presence of pathogens in a sample, the presence of a mutation, the presence of a particular length polymorphism or isozyme, the isolation of homologous sequences from different species, and the like. See the discussion in the Background section.

Usually, the sample employed will be genomic or cDNA which can be digested into a plurality of different restricted fragments by use of restriction endonucleases, generally at least two different fragments, usually five or more different fragments, and the mixture may be fifty or more or thousands or millions of different fragments. The restriction digestion may be prior to or concurrent with the mixing with the labeling moieties and ligation.

The method described above for labeling double-stranded DNA fragments with a detectable moiety covalently joining the labeled DNA to the fragments, separating sequences binding to a predetermined probe sequence and then further amplifying these sequences is very general and can be used in any situation where one wishes to amplify and or detect a particular sequence, even if the actual sequence of nucleic acids of such target has not been established.

The source of the sample may be any material or substance comprising nucleic acid. The nucleic acid need not be a naturally occurring nucleic acid, but may be synthesized chemically, enzymatically, or biologically and may have other than naturally occurring purines and pyrimidines. The sample source may be cellular or non-cellular, may be a clinical sample or isolate, may be derived from such physiological media as blood, serum, plasma, stool, pus, scrapings, washing, urine, or the like; may be associated with a set or subset of cells, such as neoplastic cells, lymphocytes, e.g., T-cells or B-cells, monocytes, neutrophils, etc.; pathogens, including viruses, bacteria, mycoplasma, fungi, protozoa, etc.; may include constructs, involving plasmid, viruses or DNA or RNA fragments, or the like. The nucleic acid sample may involve DNA, which may be chromosomal or extrachromosomal, e.g., plasmid, viruses, synthetic constructs, etc. or RNA, such as messenger RNA, transfer RNA, ribosomal RNA, viruses, or the like, where the RNA may be transcribed into dsDNA. The nucleic acid sequences may involve structural genes, untranslated regions, regulatory regions, introns, exons, or the like.

The detection may be for a wide variety of purposes. Detection may involve diagnosis of a diseased state in plant or animal species, such as neoplasia or other aberrant cellular state, the detection of sets or subsets of cells, such as lymphocytes at various stages of differentiation, the detection of strains or species of pathogens, the monitoring of genetically engineered expression, or the like.

Prior to use of the sample in the subject invention, the sample may have been subjected to a variety of chemical or physical treatments, such as proteolysis, extraction, precipitation, separation of nucleic acid from other components, such as lipids, proteins, or the like, hydrolysis of RNA, inactivation of nuclease, concentration, chromatography, dehydration, heating, etc. The sample may be manipulated for a variety of reasons, such as removal of interfering materials, preparation for storage or shipment, concentration, or the like.

The sample will normally be subjected to fragmentation by employing restriction enzymes. The restriction enzymes will cleave at the recognition site, usually, but not necessarily, having a symmetrical 4 to 8 bp, usually resulting in termini, blunt or overhangs, of known sequence. One or more restriction enzymes may be employed, normally not more than two, preferably one. Depending upon the nature of the sample for the amplification, as a result of the restriction process fragments may be provided usually varying from abut 50 bp to 200 kbp. Various restriction enzymes may be used depending upon the size of fragments desired, the nature of the sample, and the like.

In some instances, the sample may involve the reverse transcription product of messenger RNA, where the mixture may be relatively small sequences of DNA and RNA. If desired, the RNA may be hydrolyzed or digested, leaving substantially only the DNA sequences. In this manner, one would have a composition of single stranded DNA. The single stranded DNA may then be converted into dsDNA using an enzyme such as DNA polymerase.

One may provide for simultaneous restriction and ligation of the 5'-3' strand of the labeling moiety to the 5' end of the sample dsDNA as described in U.S. Pat. No. 5,093,245 or EPA 89400220.3. Thus, the restriction enzyme(s) and ligase may be combined in the same reaction mixture. Normally not more than one restriction enzyme will be used. The labeling moiety is usually designed so that it will not be capable of self ligation, e.g. by the lack of terminal phosphates, and, when the moiety is ligated to the sample dsDNA, the ligated product will not recreate the restriction enzyme recognition sequence at the site of ligation. Any sample dsDNA restriction fragments that are ligated to each other will be subsequently cleaved until a labeling moiety is ligated on to the sample dsDNA fragment. Thus, the system ensures the substantially complete cleavage and labelling of all of the restriction enzyme recognition sites in the sample DNA.

In reviewing the process of providing for the labeling moieties comprising the primer binding site joined to the termini of the sample dsDNA fragments, reference will be made to the drawings.

The labeling DNA moiety will have two-strands, one, referred to as the first 5'-3' strand, will be capable of ligation to the abutting sample strand, or may be provided by an alternative process. Either strand or both may include one or more tags or ligands, but tags or ligands are not required. In addition, the 3'-5' strand will serve as a primer binding site in the amplification reaction resulting in replication of the strand to which the 3'-5' strand is bound. Usually, each sequence will be of at least six nucleotides, usually at least eight nucleotides, and at least one sequence, usually the ligaid will be at least twelve nucleotides, and may be fifteen nucleotides or more, usually not more than one hundred nucleotides.

Because of the manner in which restriction enzymes cleave, the first strand may be readily ligated to its associated strand (adjacent 5' termini) of the dsDNA fragment as depicted in FIG. 1a. U.S. Pat. No. 5,093,245 describes various methods for performing such ligations, including situations when the restriction results in blunt ends or 3' overhangs.

Figure 1B:
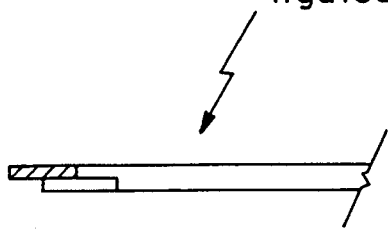
Figure 1B:
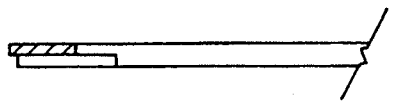

Various techniques may be employed for forming or joining the ligaid at or to the 3' termini of the dsDNA fragments. The drawings depict some of these techniques. As depicted in FIG. 1b, one method is referred to as the "fill-in" reaction, where after combination of the dsDNA with the labeling DNA moiety, the first 5'-3' strand is joined to the associated dsDNA strand by ligation. (By "associated" is intended the strands of different entities which have the bonding of the sugars in the same direction, e.g., 5'-3' or 3'-5'. Thus, the associated strands allow for ligation while maintaining the same directional order). Then, by filling in with DNA polymerase employing dNTPs, one can extend the 3' end of the dsDNA to replicate any overhang and the first strand sequence, while displacing the ligaid. In this manner, a blunt end can be obtained with a recreated ligaid.

Figure 1C:
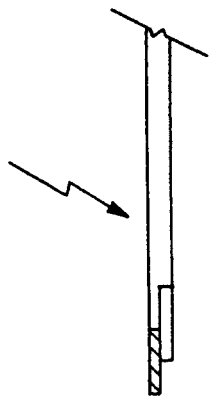
Figure 1C:
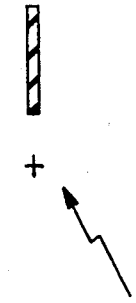
Figure 1C:
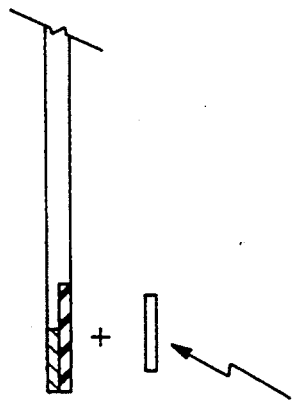

An additional way, shown in FIG. 1c, is to use a truncated ligaid as part of the labeling moiety. The truncated ligaid would be in register with the associated strand of the sample dsDNA to which the truncated ligaid is adjacent. The dsDNA and labeling moiety may have blunt or staggered ends where the ends of the different entities may be associated or in register. (In register intends that each of the ends of the strands of the labeling moiety will be adjacent to the associated ends of the dsDNA fragment strands.) After ligating the first strands to the 5' termini of the associated strands, one could then mildly denature the mixture, in the presence of a longer ligaid which would extend at least through the primer sequence, where the ligaid would have a phosphorylated 5' terminus (a 5' phosphate or triphosphate). After displacement and hybridization occurred, the temperature could be lowered and the ligaid ligated to the 3' terminus of its associated fragment strand. Alternatively, ligation could be attempted at the elevated temperature, because ligation can proceed at mildly denaturing temperatures at which the ligase enzymatic activity is not lost.

Generally, the truncated ligaid will be at least about 5 nucleotides, more usually at least about eight nucleotides, and not more than about thirty nucleotides, more usually not more than about twenty nucleotides. The phosphorylated ligaid will be at least twenty number percent larger than the truncated ligaid more usually at least about thirty number percent larger and may be one hundred number percent or greater than the truncated ligaid.

Yet another additional way to accomplish labeling is to utilize a phosphorylated ligaid in the initial ligase labeling reaction instead of the unphosphorylated ligaid. See Figure 1d. Phosphorylation of the ligaid can be achieved by using a kinase enzyme with an appropriate nucleotide triphosphate, or, preferably, it can be chemically added during ligaid synthesis. Lower yields will be encountered, based on the amount of labeling moiety in relation to the amount of labeling achieved, because ligaids will then ligate directly to first strands in a reaction that competes with the desired labeling. A low yield at this stage may be satisfactory if sufficient amplification is gained at a later stage.

The particular manner of ligation is not critical to this invention and any convenient ligating conditions may be employed for either enzymatic or chemical ligation.

The labeling moiety dsDNA will have a sequence (primer binding sequence) which will serve for hybridization to a primer sequence for use in an amplifying system. Any convenient sequence may be employed, particularly sequences which are not likely to be encountered in the sample. While as few as five nucleotides may suffice, normally at least eight nucleotides will be employed, more usually at least twelve nucleotides, and in many instances, one may employ thirty or more nucleotides. Various arbitrary sequences may be used, where the sequences will be selected to minimize binding of primers to other than the ligaid primer binding site. If desired, one may have a plurality of primer binding sites present in the ligaid, so that one may use different sequences as primers, depending upon the nature of the sample. By having a plurality of primer binding sites, one can determine which of the primer binding sites may be best suited for a particular type of sample or target DNA. Alternatively, these primer sites could be used in series to further reduce background. By providing for a primer sequence foreign to the sample DNA, a target of unknown sequence may be amplified.

Once the labeling moiety has been ligated to or filled-in adjacent to the two strands of the dsDNA fragments at both termini, the resulting primer binding site labeled fragments can be probed for the presence of a particular sequence. See U.S. patent application Ser. No. 276,139, filed Nov. 23, 1988 or EPA 88403266.5 for a discussion of possible means for selection by hybridization prior to amplification. Denaturation is usually the first step in such means for selection. The particular manner of denaturation is not critical to this invention and any technique may be employed. Elevated pH, employing a convenient hydroxide, low ionic strength, elevated temperatures, chaotropes or denaturants, may be used individually or in combination. The resulting single stranded DNA may then be probed for the presence of a target sequence of interest for isolation of hybridizing strands. A single probe may be employed, or a mixture of probes, for example, where the protein sequence is known, but the DNA is not. In this situation, one prepares a mixture of probes, based on the redundancy of the codons. Various techniques may be used to identify the strands which bind to the probe, so as to reduce the complexity of the mixture which is subsequently to be amplified. Techniques include gel electrophoresis, cesium chloride gradient centrifugation, particle separation, filtration, etc.

Of particular interest is particle separation, where the probe has a specific binding pair member, which member is a ligand or receptor, normally a ligand, or is directly linked, covalently or non-covalently, to a support which allows for separation, e.g., particles, well walls, etc. A variety of complementary specific binding pair members are available, such as biotin and avidin or streptavidin (strept/avidin), haptens and antibodies, substrate and enzymes, ligand and surface membrane protein receptors, complementary nucleic acid sequences and the like. The biotin-strept/avidin combination is of particular interest because of the high binding affinity of the pair.

The probe may be labeled in a wide variety of ways. For example, nucleotides conjugated to, or which can be conjugated to biotin or other ligands may be included during synthesis of the probe. Particles may then be conjugated with the reciprocal specific binding pair member, so that separation can be achieved by binding of the sample strands to the particles by means of the probe and the specific binding pair. Among particles, paramagnetic particles are preferred since they may be separated by means of a magnetic field. Particularly, by employing tubular vessels, the magnetic field may be used to orient the particles along the side(s) of the tubular vessel for ease of removing all of the liquid from the vessel without disturbing the particles and than washing the particles vigorously to remove non-specifically bound nucleic acid.

Once the separation and removal of non-specifically bound nucleic acids has been performed, the sample strands may be released by employing denaturation conditions or by breaking the link joining the support to the probe (e.g., reducing a disulfide link) and the liquid removed from the vessel for further processing. Alternatively, the DNA can be amplified directly off the support.

The primers may or may not be labelled, depending on the ultimate mode of detection preferred. If the primer comprises a fluorescent label, the amplification product fragment(s) will be fluorescent and can be detected on a fluorescent gel scanner or other appropriate fluorescent detection systems. Such labeling would also permit the analysis of fragments of different samples in the same lane of a gel if different fluorescent dyes were used for the amplification primers of different samples. Also, size standards with unique fluorescent labels can be run in the same lane in order to provide for in-lane size calibration. If the primer is not labeled, the strands can be identified or detected by means of a probe or probe mixture of known sequence and comprising a detectable entity or by means of some other identifying molecule, such as a fluorescent molecule, such as ethidium bromide which binds to DNA, or silver staining the DNA.

The next step is amplification, where the selected sample strands are hybridized with the primer. Since both ends of the strands have been attached to the same dsDNA labelling moiety, only a single primer is required.

The sample DNA may be amplified by any means. The particular manner of amplification is not critical to this invention, so long as the method provides for sufficient reliability and production of a large enough amount of DNA to be analyzed.

After sufficient cycles of denaturation and hybridization with the primers and primer extension, the resultant DNA may be used in a variety of ways for analysis. Where one is interested in small differences in sequences, one may denature the double-stranded DNA and probe under stringent conditions with a specific probe. Various techniques exist for identifying the presence of a single site mutation, such as hybridization using allele-specific oligonucleotide. In this manner, one may distinguish between various polymorphs, pathogen strains, or the like.

In many other cases, one may be solely interested in the size of the fragments as diagnostic of the sample. In this situation, one may employ electrophoresis, separating the fragments by size and identifying the nature of the sample by the size of the amplified DNA. In some instances, it may be useful to do restriction analysis, where one may use one or more restriction enzymes, particularly one restriction enzyme, and identify the nature of the sample by the size of the resulting fragments or the presence or absence of a particular restriction site. Other techniques may also be employed.

The following examples are offered by way of illustration and not by way of limitation.

EXPERIMENTAL

The following are exemplary labeling protocols.

Labeling Protocol

Described below is a protocol for labeling a sample of DNA with desired priming sequences when the DNA of interest is restricted with the enzyme HindIII. Analogous protocols would be used for other restriction enzymes. Note the three possible variations of Step 4.

1. Oligonucleotide of the following sequences are synthesized using a Model 381A DNA Synthesizer (Applied Biosystems, Foster City, Calif.) and standard protocols as recommended by the manufacture:
   a. The "First Strand" oligo (see FIG. 1a), with the sequence 5'GGT GTG GTT TGG TTG TGT TTG GTT GGT TTG TGG TGT T 3' (SEQ. ID. NO: 1:)
   b. The "Ligaid" oligo (see FIG. 1a), with the sequence 5'AGC TAA CAC CAC AAA C 3' (SEQ. ID. NO: 2:)
   c. The "Phosphorylated ligaid" (see FIG. 1c), with the sequence 5'p-AGC TAA CAC CAC AAA CCA ACC AAA CAC AAC CAA ACC ACA CC 3' (SEQ. ID. NO: 3:)

If desired, a fluorescent dye such as fluorescein may be added to the 5' end of the First Strand oligo to track the labeling reaction. This would be done using standard protocols for producing fluorescent labeled oligonucleotide using the Amino-Link 2 compound from Applied Biosystems. The Phosphorylated ligaid should be phosphorylated using the standard kinasing protocols (see Maniatis et al., Handbook of Molecular Biology, Cold Spring Harbor Press, 1982) or using a compound like 5' Phosphate-ON from Clontech, Palo Alto, Calif.

2. In a 1.5 ml polypropylene tube, the following items are mixed together:
   5.2 μl of a 20 picomole per μl of an aqueous solution of the First Strand oligo.
   5.2 μl of a 20 picomole per μl of an aqueous solution of the ligaid oligo.
   11.5 μl of water
   10.0 μl of a buffer which is 100 mM Tris HCl, pH 7.5, 600 mM NaCl, 70 mM $MgCl_2$, and 1 mg/ml bovine serum albumin
   5.0 μl of 20 mM ribose ATP
   3.30 μl of 300 mM dithiothreitol
   50 μl of a 200 microgram per ml aqueous solution of the DNA to be labeled
   5.8 μl of a 12 unit per μl solution of HindIII enzyme
   4.0 μl of a 2 unit per μl solution of T4 DNA ligase 3. The entire mixture is incubated at 37° C. for 4 hours, resulting in the digestion of the sample into HindIII restriction fragments that are end-labeled with the First Strand oligo on the 5' end of each strand of each restriction fragment.

4. The amplification primer binding site is then attached to the 3' end of each restriction fragment using one of the three following techniques:
   a. A fill-in protocol is accomplished by performing the following steps:
      i. add the four deoxynucleotide triphosphates (A, T, C and G) to a final concentration of 200 μM each to the labeling mixture described above following the incubation step.
      ii. Klenow polymerase I is added to the mixture, using 1.5 units of enzyme per μg of DNA being labeled.
      iii. Incubate for 10 minutes at 37° C. The reaction is then stopped with addition of EDTA to a final concentration of 20 mM or by freezing.
   b. A displacement protocol is accomplished by performing the following steps:
      i. 6.5 μl of a 20 picomole per μl aqueous solution of the Phosphorylated ligaid (see step 1) is added to the labeling mixture following the initial restriction/ligation incubation.
      ii. Heat the resulting mixture to 50° C. for 10 minutes to destabilize the Ligaid oligo and have it displaced by the phosphorylated ligaid which will bind to the first strand, abutting the 3' end of each strand of the restriction fragment.
      iii. Continue the ligation procedure at 37° C. for 30 minutes. Sufficient ligase activity should still exist from the step 3 incubation to allow ligation of the Phosphorylated ligaid to 3' end of each strand of the restriction fragment; if not, additional ligase can be added.
   C. a direct labeling protocol is accomplished by substituting the Phosphorylated ligaid for the Ligaid oligo in step 2 above. This direct labeling protocol is useful if inefficient labeling can be tolerated.

5. The labeled reaction products can then be used in the next step (typically the hybridization and selection protocol) or else stored for future use at 4° C.

The following is an exemplary protocol for hybridization and selection of sample DNA.

Hybridization/Selection

After the sample has been labeled with the desired priming sequences, a probe is used to select out those particular fragments in the sample that contain sequence homologous to the probe. Described below is an exemplary protocol for the hybridization and selection process:

1. Biotinylated probe is made using a variant of the protocol described above for ligating on priming sequences. The following mixture is prepared:
   14.0 μl of 25 picomoles/μl biotinylated oligo (synthesized with the sequence 5' TNN NTT TTT TTT TTT TCA GTT ATG ATG TTG T 3', (SEQ. ID. NO: 5:), where N is a linker arm nucleotide (Molecular Biosystems, Inc., San Diego, Calif.) to which biotin N-hydroxysuccinimide is coupled).
   14.0 μl of 25 picomoles/μl of a complementary oligonucleotide (synthesized with the sequence 5' ACA ACA TCA TAA CTG AAA 340 ) (SEQ. ID. NO: 6:)
   60 μl of water
   13.0 μl of 10X Restriction Enzyme Buffer A (Boehringer Mannheim, Indianapolis, Ind.)
   6.5 μl of 20 mM ATP
   10.0 μl of 1 μg/μl of purified probe DNA to be labelled, e.g., if a probe for the plasmid pSP64 is made, purified pSP64 DNA is used.
   10.0 μl of AluI restriction enzyme (@8 units/μl)
   3.5 μl of T4 DNA ligase (@3 units/μl)

The total reaction volume of 130 μl is incubated for 4 hours at 37° C. and then quenched with the addition of 6.5 μl of 0.2M EDTA.

2. Streptavidin coated paramagnetic particles are prepared from biotinylated particles (Advanced Magnetic Cambridge, Mass.;) 20 ml of the commercial particles at 5 mg/ml are washed and then resuspended at 5 mg/ml in 500 mM HEPES, pH 7.8 with 0.25% Tween-20. 0.1 ml of a 25% solution (w/v) of succinic anhydride in dimethylformamide is added to each ml of particle suspension. The mixture is placed on ice for 15 minutes, shaken, and then put on a shaker bath at 37° C. for 60 minutes. The particles are magnetically separated, supernatant is removed and then the particles are resuspended with a buffer which is 10 mM sodium phosphate, pH 7.4, 0.15M sodium chloride, 1 mM EDTA, and 0.25% Tween-20. This separation, supernatant removal and resuspension process (a "wash") is then repeated two more times and then the particles are resuspended at 5 mg/ml in the same buffer. (This buffer is referred to as 1X SSPE plus 0.25% Tween-20). 0.1 ml of a 10 mg/ml solution of streptavidin in the same phosphate buffer is then added to each ml of the particle suspension. The particles are then shaken at 30° C. for one hour, magnetically separated, and then washed three more times with 1X SSPE plus 0.25% Tween-20 and finally resuspended in this buffer at 5 mg/ml of particles and stored at 4° C. Just prior to use, the particles are washed with 1X SSPE plus 1.% Tween-20 followed by a wash in 160 mM sodium carbonate, pH 10.2 with 1.0% Tween-20, (referred to as the alkaline wash buffer), and finally resuspended to a concentration of 5 mg/ml in the alkaline wash buffer. Alternatively, M280 streptavidin Dynabeads, Dynal Great Neck, N.Y., may be used as the particles and do not require the above derivitization steps.

3. A two-part hybridization mixture is prepared as follows:

3a. Solution A—115 ml of 1.0M sodium carbonate is mixed with 29 ml of 1.0M sodium hydroxide and 43 ml of 0.2M trisodium EDTA.

3.b. Solution B—557 ml of 9.0M sodium perchlorate is mixed with 257 ml of a 51.5% (w/v) aqueous solution of sodium polyacrylate. (The sodium polyacrylate solution is prepared by slowing adding 50% (w/w) NaOH into 65% polyacrylic acid (Aldrich, Milwaukee, Wis.) on ice until a diluted solution gives a pH of 8.0 to 8.5).

4. The hybridization mix is prepared by combining 10 µl of solution A and 60 µl of solution B and then adding the following:

10 µl of biotinylated probe, prepared as above and diluted to 100 femtomoles of biotinylated ends per µl.

100 µl of the DNA (which has been labeled with the priming sequences as described previously) at a concentration of about 0.1 µg/µl.

5. The solution is then mixed well, incubated at 90° C. for 15 minutes to denature the DNA, and then incubated for 15 minutes at 47° C. to allow hybridization to occur.

6. After cooling to 37° C., 40 µl of the streptavidin coated particles are added, mixed in the DNA solution, and allowed to incubate for 15 minutes at 37° C.

7. The particles are then pulled to one side of the 1.5 ml Eppendorf tube with a magnet, the supernatant is removed, and the particles are resuspended with fresh alkaline wash buffer at 60° C. This washing procedure is then done five more times. A final wash is then done in 100 mM NaCl with 0.5% Tween-20 at room temperature, supernatant is removed, and the particles are ready for the amplification steps.

Amplification

In preparation for the amplification step, the primer sequence, 5' G TTT GGT TGG TTT GTG GTG T (SEQ. ID. NO: 4:), is synthesized and diluted to a concentration of 10 picomoles/µl in water. An exemplary protocol for the amplification of the labeled DNA which has been selected by the probe and bound to the particles is performed as follows:

1. The particles are resuspended in 70 µl of water and 20 µl of 25% chelex in water, allowed to incubate for 10 minutes as follows:

2. The particles are magnetically pulled to the side of the tube and 20 µl of the supernatant is then mixed with the following:
28.5 µl H$_2$O 10 µl of buffer which is 100 mM Tris-HCl, pH 8.4, 500 mM KCl, 15 mM MgCl$_2$, 1 mg/ml gelatin (Perkin Elmer-Cetus 10× Amplification Buffer)

1.0 µl of 10 mM MgCl$_2$

12 µl of a mixture containing the deoxynucleotides dATP, dCTP, dGTP and dTTP, each at a concentration of 2.5 mM.

24 µl of the 10 picomole/µl solution of the amplification primer described above.

The mixture is then overlayed with mineral oil in a 500 µl polypropylene tube and heated to 90° C. Then, 5 units of Taq polymerase (1 µl) is added and mixed into the aqueous solution.

3. Samples are placed in a Perkin Elmer-Cetus Thermal Cycler and amplified using 25 of the following cycles: 94° C. for 1 minute for denaturation, 65° C. for 2 minutes of annealing, and 72° C. for 6 minutes for extension. A 5 µl aliquot of the sample is then taken, 2 µl of 15% Ficoll loading buffer is added, and the amplification products are loaded onto a 0.8% agarose gel for separation and detection. The gel is run for 4 hours at 3 volts/cm using TBE running buffer including ethidium bromide at 0.1 µg/ml in the buffer and gel for staining the DNA. The particular band or bands corresponding to the fragment length(s) which are selected by the probe are then detected. Actual detection may be visual or with the use of a fluorescence gel scanner. In the case of the probe being pSP64 prepared as described above and the specific target being pSP64 in a sample cut by Hind III enzyme, the detected band would be 3.0 kilobases long.

In accordance with the subject invention, numerous advantages are achieved. The requirement for high efficiency at individual steps in order to detect rare sequences is substantially reduced. Smaller amounts of sample are required. A single oligo primer binding site is employed, so that only one primer needs to be used during each cycle of the amplification. The protocols may be automated using conventional materials, whereby technician error may be substantially minimized and higher sensitivities and accuracy achieved. By employing purified sequences, longer strands may be copied with higher fidelity. The subject method provides for amplification of DNA where the sequence of the target DNA may be only partially known or unknown.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for amplifying dsDNA comprising a target sequence., said method comprising:
   combining a dsDNA sample with labeling DNA moieties in registry with termini of restriction fragments of said sample dsDNA, wherein said labeling DNA moieties comprise at least one primer binding site sequence, said labeling DNA moieties comprise a 5'-3' first strand and a ligaid or truncated ligaid strand, at least partially complementary to said first strand, and said restriction fragments are formed prior to, during, or after said combining;
   covalently joining both strands of the labeling DNA to the associated strands of said dsDNA in register, with the proviso that said truncated ligaid may be displaced or substituted with a ligaid strand comprising said primer binding site sequence prior to said covalent joining;
   denaturing said dsDNA labeled strands to produce labeled single stranded DNA comprising a primer binding site sequence proximal to the 3'-terminus of said labeled single stranded DNA and complementary sequence on the 5'-terminus;
   substantially separating any single stranded labeled DNA comprising said target sequence from single stranded labeled DNA lacking said target sequence; and
   amplifying said single stranded labeled DNA comprising said target sequence employing primers complementary to said primer binding site sequence.

2. A method according to claim 1, wherein said covalently joining comprises:
   ligating said first strands to the 5'-termini of said dsDNA fragment strands to produce a first strand ligated product;
   removing said ligaid strand by displacement;
   extending the 3'-termini of said dsDNA strands to produce said ligaid sequences complementary to said first strand sequences.

3. A method according to claim 1, wherein said covalently joining comprises:
   ligating said first strands to the 5'-termini of said dsDNA fragment strands to produce a first strand ligated product;
   displacing said ligaid or truncated ligaid strand by denaturation and hybridization with a second ligaid strand, wherein said second ligaid strand is phosphorylated at the 5'-terminus not later than before ligating; and
   ligating said ligaid to the 3'-terminus of said dsDNA strands in registry with said ligaid strand.

4. A method according to claim 1, wherein said labeling moieties comprise a ligaid phosphorylated at the 5'-terminus, and said phosphorylated ligaid is ligated to the dsDNA strand in registry with said ligaid.

5. A method according to claim 1, comprising the additional step of:
   separating said amplified dsDNA by size to identify the size of the dsDNA fragment comprising said target sequence.

6. A method according to claim 1, wherein said separation is by means of paramagnetic particles, wherein said labeled single strands are non-covalently bound to said paramagnetic particles.

7. A method according to claim 6, wherein said separation is by means of a probe complementary to said target sequence and comprising biotin and said paramagnetic particles comprise strept/avidin.

8. A method for amplifying dsDNA comprising a target sequence, said method comprising:
   combining a dsDNA sample with labeling DNA moieties in registry with termini of restriction fragments of said sample dsDNA, wherein said labeling DNA moieties comprise at least one primer binding site sequence, said labeling DNA moieties comprise a first 5'-3' strand and a ligaid or truncated ligaid strand, at least partially complementary to said first strand, and said restriction fragments are formed prior to, during, or after said combining;
   covalently joining both strands of the labeling DNA to the associated strands of said dsDNA in register, with the proviso that said truncated ligaid may be displaced or substituted with a ligaid strand comprising said primer binding site sequence prior to said covalent joining;
   denaturing said dsDNA labeled strands to produce labeled single stranded DNA comprising a primer binding site sequence proximal to the 3'-terminus of said labeled single stranded DNA and complementary sequence on the 5'-terminus;
   substantially separating any single stranded labeled DNA comprising said target sequence from single stranded labeled DNA lacking said target sequence by hybridizing said single stranded labeled DNA with a probe having a nucleic acid sequence complementary to said target sequence and comprising a member of a specific binding pair to produce probe bound strands, combining said probe bound strands with the complementary member of said specific binding pair bound to a solid support, and separating single stranded labeled DNA bound to said support from unbound single stranded labeled DNA; and
   amplifying said single stranded labeled DNA comprising said target sequence employing primers complementary to said primer binding site sequence.

9. A method according to claim 8, wherein said solid support is paramagnetic particles.

10. A method according to claim 8, wherein said ligaid or truncated ligaid is displaced with a ligaid comprising said primer binding site sequence and phosphorylated at the 5'-terminus.

11. A method for amplifying dsDNA comprising a target sequence, said method comprising:

combining a dsDNA sample with labeling DNA moieties in registry with termini of restriction fragments of said sample dsDNA, wherein said labeling DNA moieties comprise at least one primer binding site sequence, said labeling DNA moieties comprise a first 5'-3' strand and a ligaid or truncated ligaid strand, at least partially complementary to said first strand, and said restriction fragments are formed prior to, during, or after said combining;

covalently joining both strands of the labeling DNA to the associated strands of said dsDNA in register, with the proviso that said truncated ligaid may be displaced and substituted with a ligaid strand comprising said primer binding site sequence prior to said covalent joining;

denaturing said dsDNA labeled strands to produce labeled single stranded DNA comprising a primer sequence proximal to the 3'-terminus of said labeled single stranded DNA and its complementary sequence 5' to said single stranded DNA;

substantially separating any single stranded labeled DNA comprising said target sequence from single stranded labeled DNA lacking said target sequence by hybridizing said single stranded labeled DNA with a probe having a nucleic acid sequence complementary to said target sequence and comprising a solid support to produce probe bound strands, and separating single stranded labeled DNA bound to said support from unbound single stranded labeled DNA; and amplifying said single stranded labeled DNA comprising said target sequence employing primers complementary to said primer binding site sequence.

12. A method according to claim 11, wherein said solid support is paramagnetic particles.

13. A method according to claim 11, wherein said ligaid or truncated ligaid is displaced with a ligaid comprising said primer sequence and phosphorylated at the 5'-terminus.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: unknown ( i i ) MOLECULE TYPE: Oligomer DNA ( x i ) SEQUENCE DESCRIPTION: SEQ ID NO:1:

GGTGTGGTTT GGTTGTGTTT GGTTGGTTTG TGGTGTT                                37

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: Oligomer DNA ( x i ) SEQUENCE DESCRIPTION: SEQ ID NO:2:

AGCTAACACC ACAAA                                                                    15

( 2 ) INFORMATION FOR SEQ ID NO:3:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: Oligomer DNA ( x i ) SEQUENCE DESCRIPTION: SEQ ID NO:3:

AGCTAACACC ACAAACCAAC CAAACACAAC CAAACCACAC C                            41

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligomer DNA ( x i ) SEQUENCE DESCRIPTION: SEQ ID NO:4:

GTTTGGTTGG TTTGTGGTGT                                                      20

( 2 ) INFORMATION FOR SEQ ID NO:5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: Oligomer DNA ( x i ) SEQUENCE DESCRIPTION: SEQ ID NO:5:

TNNNTTTTTT TTTTTTCAGT TATGATGTTG T          31

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligomer DNA ( x i ) SEQUENCE DESCRIPTION: SEQ ID NO:6:

ACAACATCAT AACTGAAA  18